United States Patent [19]

Honig et al.

[11] Patent Number: 5,253,774
[45] Date of Patent: Oct. 19, 1993

[54] REAGENT RECEPTACLE AND SUPPORT RACK FOR AUTOMATED CLINICAL ANALYZERS

[75] Inventors: Jordan S. Honig, Albany; Christopher J. Macko, Martinez; Richard B. Edwards, Vacaville, all of Calif.

[73] Assignee: Bio-Rad Laboratories, Inc., Hercules, Calif.

[21] Appl. No.: 904,915

[22] Filed: Jun. 26, 1992

[51] Int. Cl.⁵ .................... B65D 43/12; B65D 51/20
[52] U.S. Cl. .................... 220/345; 220/258; 220/346; 215/247; 215/322; 215/347; 211/126
[58] Field of Search .......... 215/100 R, 101, 232, 215/247, 249, 277, 280, 286, 322; 220/254, 258, 322, 323, 345, 346, 351, 359; 211/126, 162

[56] References Cited

U.S. PATENT DOCUMENTS

| | | | |
|---|---|---|---|
| 2,436,297 | 2/1948 | Guarnaschelli | 215/322 |
| 3,463,339 | 8/1969 | McGuckin | 215/247 |
| 3,499,568 | 3/1970 | Vinas Riera | 215/247 X |
| 3,637,102 | 1/1972 | Shaw | 215/247 |
| 3,726,767 | 4/1973 | White | 220/345 X |
| 3,814,582 | 6/1974 | Rohrbaugh | 23/230 R |
| 3,832,135 | 8/1974 | Drozdowski | 23/253 R |
| 3,942,630 | 3/1976 | Phillips | 220/346 X |
| 4,054,415 | 10/1977 | Seligson | 23/253 R |
| 4,063,395 | 12/1977 | Stewart et al. | 220/444 X |
| 4,138,026 | 2/1979 | Conklin | 215/12.2 |
| 4,235,840 | 11/1980 | Mendoza | 422/64 |
| 4,254,884 | 3/1981 | Maruyama | 215/232 |
| 4,577,474 | 3/1986 | Peterson | 220/903 X |
| 4,744,614 | 5/1988 | Gombosi | 220/345 X |
| 4,789,074 | 12/1988 | Han | 215/347 |
| 4,939,095 | 7/1990 | Yokotani | 436/47 |
| 4,961,906 | 10/1990 | Andersen | 422/102 |
| 5,061,263 | 10/1991 | Yamazaki et al. | 215/247 X |
| 5,066,135 | 11/1991 | Meyer | 366/208 |
| 5,084,242 | 1/1992 | Sakuma | 422/100 |
| 5,088,612 | 2/1992 | Storar et al. | 215/247 |
| 5,129,538 | 7/1992 | Bennett | 220/346 |

FOREIGN PATENT DOCUMENTS 57-16360 1/1982 Japan.
61-247974 11/1986 Japan.

Primary Examiner—Allan N. Shoap
Assistant Examiner—Vanessa Caretto
Attorney, Agent, or Firm—Townsend and Townsend Khourie and Crew

[57] ABSTRACT

A reagent vessel and support rack for use in an automated clinical analyzer are disclosed. Characteristic features of the vessel are a membrane covering which is puncturable and preferably self-sealing, and characteristic features of the support rack are a rigid wall and retaining members to hold the vessel in the rack with the membrane against the rigid wall of the rack, thereby providing structural support to the membrane, with holes in the wall to permit access to the membrane and hence to the contents of the receptacle.

1 Claim, 3 Drawing Sheets

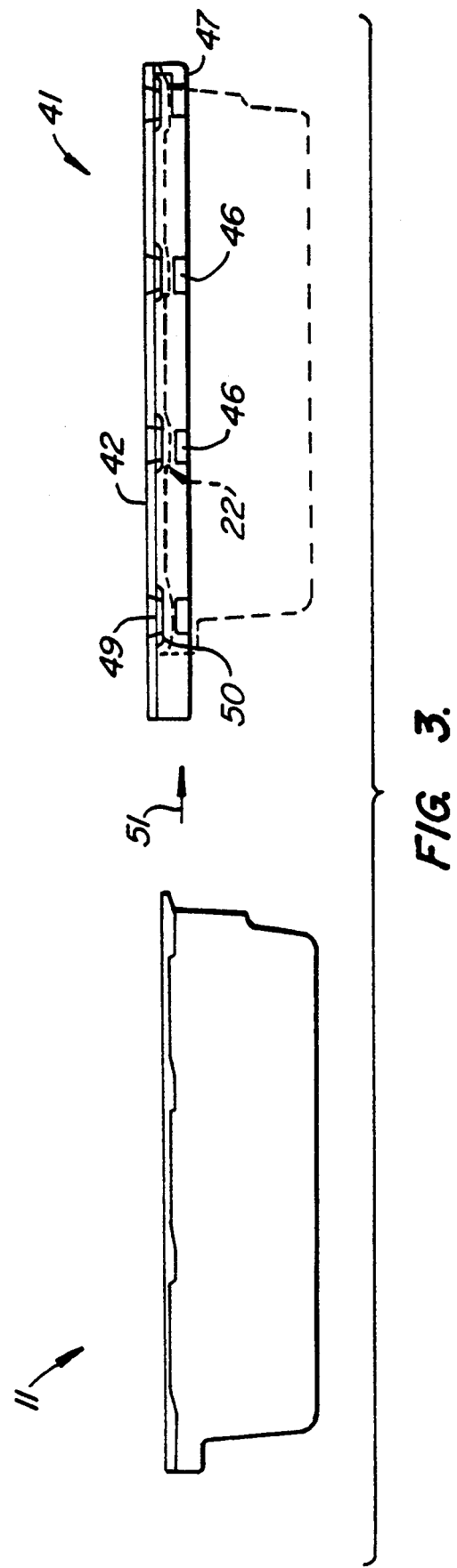

REAGENT RECEPTACLE AND SUPPORT RACK FOR AUTOMATED CLINICAL ANALYZERS

This invention lies in the field of apparatus for clinical assays, and particularly for automated apparatus for multiple assays of small volume clinical samples, with particular emphasis on sealed receptacles for liquid reagents.

BACKGROUND OF THE INVENTION

Immunoassays and similar diagnostic procedures are of major importance in health care and clinical research. Many clinical laboratories perform a large number of such procedures on a routine basis, which involves the handling of a multitude of samples, reagents, and microtiter wells and a large number of repetitions of steps and procedures. The development of automated analyzers has reduced the opportunities for human error and improved the efficiency, accuracy and reliability of these procedures, with consequential reductions in cost. One example of an automated analyzer of this type is the analyzer disclosed in co-pending, commonly owned U.S. patent application Ser. No. 07/732,858, filed Jul. 19, 1991, entitled "Automated Clinical Analyzer," Christopher J. Macko, Donald R. Flory and Jordan S. Honig, inventors. An additional application of potential interest for its disclosure of related equipment is co-pending, commonly owned U.S. patent application Ser. No. 07/732,861, filed Jul. 19, 1991, entitled "Rack-Suspendable Carrier for Clinical Assay Wells With Removable Lid," Jordan S. Honig, inventor. Both such applications are incorporated herein by reference.

The analyzer disclosed in Ser. No. 07/732,858 and others of similar function use various types of assay reagents arranged in combinations, each combination containing the reagents required for a single assay, with sufficient quantities of each reagent so that the assay can be performed on a multitude of samples. Since the reagents are held in troughs or other receptacles from which aliquots are drawn by automated pipets, such arrangements raise a number of concerns. One concern is the exposure of the reagents to the environment during the periods of time between aliquot withdrawals. Certain reagents are susceptible to chemical change when left in open containers. Another concern is the evaporation of solvents from the reagents. This causes an increase in the reagent concentration, which is not compensated for by the automated pipetting. The result is a loss of accuracy and reproducibility in the assay results.

SUMMARY OF THE INVENTION

These and other concerns are addressed by the present invention, which resides in the combination of a reagent receptacle with a membrane which is puncturable, and preferably self-sealing upon puncture, and a separate support structure capable of holding one or more such receptacles, the receptacle(s) being mounted in the support structure prior to placement of the receptacles in an automated analyzer where they are used in a repeated series of assays. The receptacle shown and discussed in detail in this specification is trough-shaped, with the membrane sealing the open top of the trough. The receptacle may be of any shape, however, with the membrane covering any surface portion of the receptacle and in any orientation so long as it can be pierced by a device such as a syringe needle to extract an aliquot. The shape of the receptacle and the size and orientation of the membrane will vary with the configuration of the analyzer for which the receptacle and support are designed and the manner in which they are held in the analyzer.

The support is a structure serving as a rack, bracket, brace or frame to hold the receptacle or two or more such receptacles. In various embodiments of the invention, the support serves one or more of several functions. One such function is to join two or more receptacles together, each receptacle containing one of the various reagents necessary for an assay procedure. Another function is to provide the structural means by which the receptacles are inserted in the automated analyzer and guided into the appropriate location. A still further function is to provide a rigid wall which is part of the support structure and which is held against the membrane, protecting the membrane against rupturing by accidental puncture and providing it with support to prevent bursting upon exposure to a reduced external pressure. The rigid wall contains one or more holes to provide access to the membrane surface so that a pipette tip can penetrate the membrane and draw a measured volume of reagent from the receptacle. The rigid wall also aids in the clamping of the membrane to the receptacle, particularly around the area which is to be penetrated by the pipette tip.

The membrane itself may be any material which is substantially impermeable to vapors generated by evaporation in the receptacle, and which can be punctured by a hypodermic syringe or pipette and will reseal once the syringe or pipette is withdrawn.

These and other features of the invention are explained in detail below and depicted in the attached drawings.

BRIEF DESCRIPTION OF THE DRAWINGS

FIGS. 1b and 1c are exploded views, showing the membrane separated from the receptacle.

FIG. 2a is a top view, and FIG. 2b is an enlarged view of a portion of FIG. 2a, shown in partial cutaway.

FIG. 3 is a side view of the receptacle of FIGS. 1a, 1b and 1c and the support of FIGS. 2a and 2b being joined together. The support is shown in cross section, taken along the line 3—3 of FIG. 2a.

DETAILED DESCRIPTION OF THE INVENTION AND PREFERRED EMBODIMENTS

The structure, function and operation of the invention as a whole may be understood by a detailed examination of one specific embodiment of the invention, even though it will be understood that this is but one example within the scope of the invention. The Figures attached hereto depict one such embodiment.

Figure 1A:
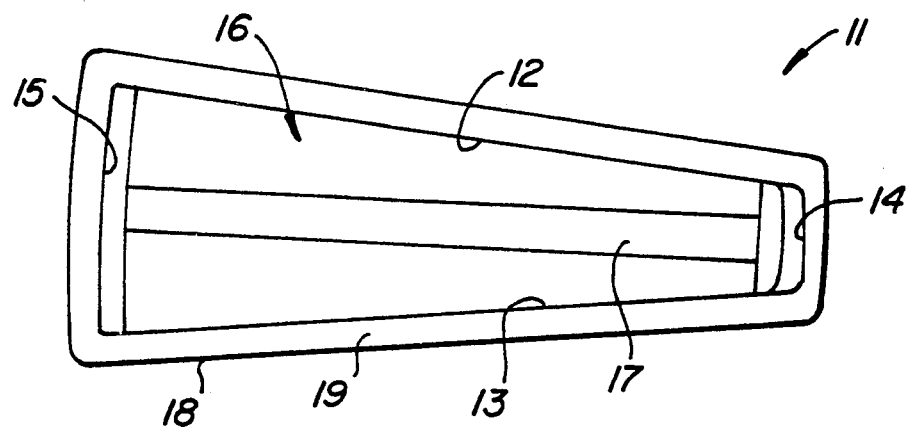
FIGS. 1a, 1b and 1c depict one embodiment of a membrane-sealed reagent receptacle in accordance with the present invention, FIG. 1a being a top view, FIG. 1b a side view and FIG. 1c an end view.
Figure 1B:
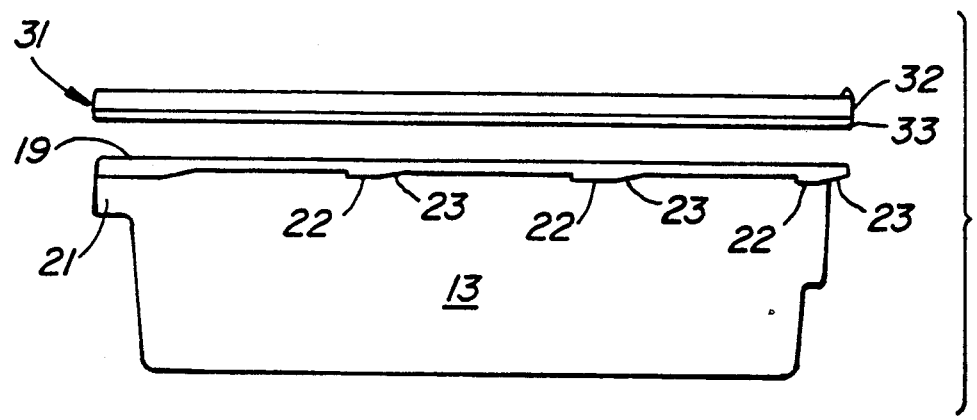
Figure 1C:
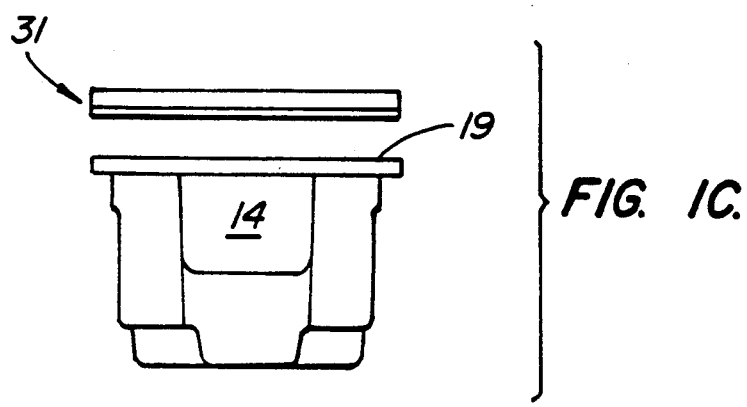

The reagent receptacle of this example is shown in FIGS. 1a, 1b and 1c. The top view of FIG. 1a shows that the receptacle 11 is trapezoidal in shape, with angled side walls 12, 13 and a front wall 14 which is narrow relative to the broader rear wall 15. The trapezoidal shape permits the receptacle 11 to be placed beside similar receptacles to form an arc of a circle. This shape is designed for use in a carousel-type analyzer, in which the reagents, samples and reaction wells are mounted in one or more carousels which rotate past functional stations at fixed positions in the analyzer. Functions performed at these stations include aliquot withdrawal and addition, well washing, detection, and any other operations required for a complete assay. The direction and degree of rotation and the amount of time spent at any particular station is programmed in such an analyzer to meet the needs of the assay. For other analyzer configurations, the receptacle may assume any shape, depending on how the receptacle is inserted into and held by the analyzer.

The receptacle 11 is a trapezoidal trough which is open at the top 16, with a narrow parallel-sided trough 17 on the bottom surface along the center line of the receptacle, for drainage of the receptacle contents to achieve efficient withdrawal. Surrounding the upper perimeter of the receptacle is a lip 18 in the form of a flat ledge. The edges of the membrane, discussed in detail below, are secured to the upper surface 19 of this ledge so that the membrane spans the entire open top 12 of the receptacle. The side view of FIG. 1b and the end view of FIG. 1c show that the lip is a flange outwardly protruding along the sides and front of the receptacle. Along the rear of the receptacle, the surface 19 forms the upper surface of a thicker finger grip 21 which facilitates the handling of the receptacle and its insertion into the support, which is described in detail below.

Figure 2A:
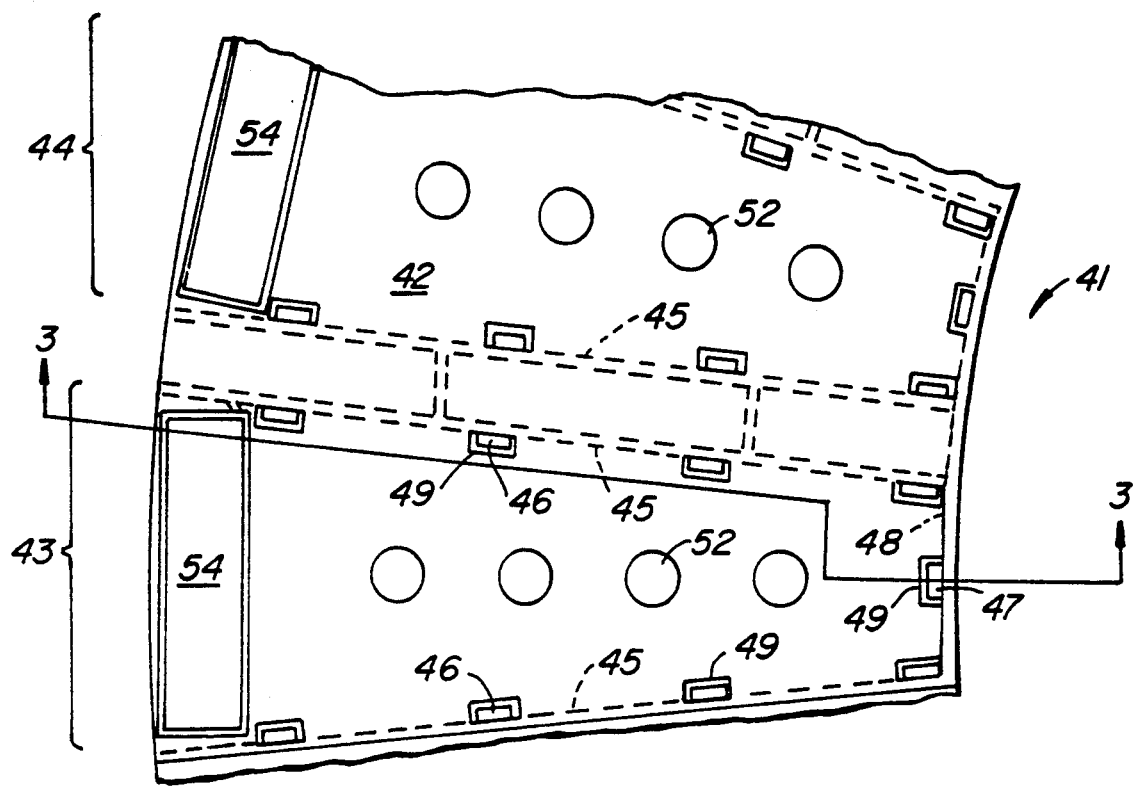
FIGS. 2a and 2b are views of a support designed to hold two or more receptacles of the construction shown in FIGS. 1a, 1b and 1c.
Figure 2B:
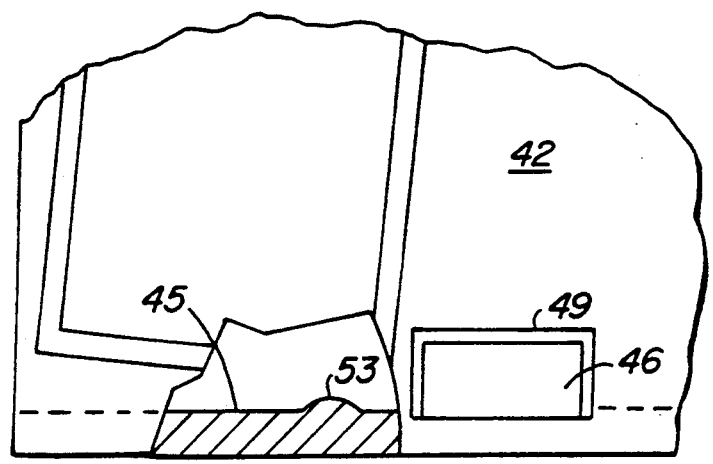

When the receptacle is fitted into the support, the portion of the lip 18 which extends along the sides and front of the receptacle slides along tabs in the support, which are shown in FIGS. 2a and 2b and discussed in detail below. The lip and tabs thus serve to guide the placement of the receptacle and hold it in position. On the underside of the lip along the sides of the receptacle are raised lands 22, visible in FIG. 1b, with sloping leading edges 23. These lands 22 are positioned in locations which correspond to the those of the tabs, providing a snug fit between the receptacle and the support at each tab. The sloping leading edges 23 permit the lands to be eased into position.

FIGS. 1b and 1c also show the membrane 31 above the upper surface 19 of the lip. The membrane 31 in this example has a trapezoidal shape identical to that of the outer perimeter of the lip 19, and is shown separated from the lip for purposes of clarity. The membrane may be any material which is substantially impermeable to vapors which might be generated by evaporation of the liquid contents of the receptacle, and yet is capable of being punctured by a sharp implement. Preferably, the membrane leaves at most a small hole after withdrawal of the puncturing implement, so that evaporation of liquid from the receptacle is reduced significantly. Most preferably, the membrane is one which reseals itself after the implement is withdrawn. Examples of self-sealing materials are natural and synthetic rubbers and many other kinds of resilient materials capable of being formed into sheets. Closed-cell foam plastics are particularly suitable.

The membrane shown in FIGS. 1b and 1c is a composite membrane consisting of two layers of material, the upper layer 32 being a closed-cell foamed polymer and the lower layer 33 a continuous polymer film. The continuous film lower layer 33 serves to provide an extra barrier to evaporation of the receptacle contents prior to use, as opposed to in between uses. The lower layer also provides a smooth lower surface which can be easily adhered to the upper surface 19 of the lip. The lower layer may be used alone, since it has a self-sealing character of its own, but preferably the self-sealing character of the membrane is enhanced by the combination of this layer with the upper layer. While a wide variety of materials may be used for the two layers, one particular example which has been found effective is an upper layer of closed-cell polyethylene foam, 1/16-inch (0.16 cm) thick, with a density of about 1-1.7 pounds per cubic feet (16-27 kilograms per cubic meter), and a lower layer of a combination of nylon (polyamide) and saran (polyvinylidene chloride), 0.003 inch (76 microns) in thickness. The membrane may be secured to the lip surface by any conventional means, depending on the materials involved, including heat sealing and adhesives. The seal may cover the entire perimeter of the receptacle or only a portion of the perimeter. Polypropylene is an example of an adhesive which may be successfully used with a polyethylene/nylon-saran membrane.

FIG. 2a is a top view of the support 41. Supports in accordance with this invention are designed to hold at least one, and preferably two or more, receptacles 11. The support shown in FIG. 2a contains a flat plate 42 which serves as a retaining wall, with regions of the plate designated as receptacle areas, two of which 43, 44 are visible, each designed to receive and retain one receptacle of the configuration shown in FIGS. 1a, 1b and 1c. The structure visible in FIG. 2a is merely a portion of the support, however. The support further contains additional areas of identical construction adjacent to these two.

The side boundaries of the receptacle areas are defined by reinforcement ribs 45 on the underside of the support extending downward (and, for this reason, shown in dashed lines). Extending inwardly from the reinforcement ribs 45 are the tabs 46 referred to above. An end tab 47 extending inwardly from a circumferential reinforcement rib 48 at the inward end of the receptacle area mates with the front end portion of the lip. The tabs 46 are at a level below that of the flat plate 42 (when the plane of the Figure is horizontal), but are visible through openings 49 directly above them in the flat plate 42. As the lip 19 of the receptacle 11 (FIGS. 1a—1c) slides over the side tabs 46 until it covers the end tab 47, the lip is visible through the openings 49 in the flat plate 42.

The insertion of the receptacle into the support is shown in FIG. 3. The receptacle 11 is shown in a side view identical to that of FIG. 1b, while the support 41 is shown in a cross-section view taken along the line 3—3 of FIG. 2a. Insertion is achieved by movement of the receptacle 11 in the direction of the arrow 51. The receptacle as inserted is shown in dashed lines. The raised lands 22 are in contact with the side tabs 46, which push the membrane covering the top opening of the receptacle up against the flat plate 42 of the support. This assures a vapor-tight barrier around the perimeter of the trough. A raised lip 50 around the underside of each of the openings 49 assures a water-tight barrier around the perimeter of the puncture.

As noted above, the configuration depicted in the drawings is merely an example of an embodiment of the invention. The lip and tabs may be replaced by a host of equivalent structures and arrangements. The lip may for example be on the support rather than the receptacle, extending inward from the reinforcement ribs to form a laterally opening groove underneath the flat plate, with the tabs being on the receptacle and extending outward, rather than on the support as shown. As a further example, the tabs may be replaced by a continuous ledge, forming a tongue and groove arrangement. Still further, snap or screw-type fittings may be used. Other examples will be readily apparent to those skilled in the art.

Returning to FIG. 2a, the flat plate 42 of the support contains a series of holes 52 in each of the receptacle areas 43, 44. Each hole provides access to the membrane of the receptacle underlying the hole, so that the membrane can be penetrated by a puncturing device such as a hypodermic needle at the end of an automated pipette for removal of reagent. The size, number and arrangement of the holes is not critical, and will generally complement the arrangement of the pipettes in the analyzer for which the support and receptacle are designed to be used. In most cases, any one hole will have an opening which represents from about 5% to about 15% of the area of the membrane covering the receptacle. In the support shown in FIG. 2a, multiple holes are present to permit several identical assays to be conducted simultaneously on different samples.

FIG. 2b is an enlarged view in partial cutaway of an outer corner of the support, i.e., the corner at the lower left in the view shown in FIG. 2a. The cutaway section shows the reinforcement rib 45 which serves as a radial boundary of the receptacle area. On the inside surface of this reinforcement rib 45 is a protrusion 53 in the shape of a rounded ridge, whose profile is seen in the figure. When the receptacle is inserted into the receptacle area, it passes this protrusion, and as the receptacle approaches the fully inserted position, the side edge of the lip 18 contacts this protrusion 53 and an identical protrusion similarly situated on the opposing reinforcement rib, pressing against both (the opposing protrusion is not shown in any of the drawings. A small degree of resiliency in the construction materials permits the receptacle to be pushed past these protrusions, and when the receptacle is fully inserted the lip is clear of both protrusions. The protrusions thus serve as a catch for holding the receptacle in the desired position in the support, preventing slippage. The protrusions also provide the user with the snap sensation when the parts are properly joined. As with the other features of the invention, alternative structures serving the function of a catch may also be used, such as mated protrusions and indentations, or catches in general on different surfaces, such as on the lip or the underside of the flat wall of the support. Further possibilities will be readily apparent to those skilled in the art.

A further feature of the support 41 shown in FIG. 2a is a delineated area 54 on the upper surface of the support, adjacent to the outer (wide) end. This area may contain machine-readable or user-readable information for use in identifying the receptacle, its contents and its intended use. The information may for example be in the form of a bar code, a magnetic code or other forms of machine-readable signals. The information may include an identification of the assay for which the reagent is intended, the reagent itself and a lot number, and an expiration date. The information may be read by appropriate reading devices on the automated analyzer itself, as a means of checking the reagent before the analyses are begun, or of determining the location of specific reagents relative to each other in the apparatus, and the information may be entered into the program driving the analyzer. Other useful types of information, uses for such information and means of manipulating such information will be readily apparent to those skilled in clinical analyses.

The foregoing is offered primarily for purposes of illustration. It will be readily apparent to those skilled in the art that the structures, shapes, materials of construction, arrangement of parts, and other parameters of the system described herein may be further modified or substituted in various ways without departing from the spirit and scope of the invention.

What is claimed is:

1. A device for holding liquid materials used in clinical assays, said device comprising:
   at least two receptacles, each having an opening;
   a puncturable membrane sealing each said opening to substantially prevent evaporation from said receptacle;
   a support to receive said at least two receptacles: and said support including for each said receptacle:
   a retaining wall whose perimeter defines an area at least as great as that of said opening, said retaining wall containing at least one hole having an area substantially smaller than said puncturable membrane; and
   guide means to guide said receptacle into said support such that said retaining wall overlies said puncturable membrane, thereby permitting puncture of said puncturable membrane through said hole.

* * * * *